(12) United States Patent
Matsuoka et al.

(10) Patent No.: US 11,957,188 B2
(45) Date of Patent: Apr. 16, 2024

(54) WEARABLE DEVICE, AND SENSOR DEVICE

(71) Applicant: Nippon Telegraph and Telephone Corporation, Tokyo (JP)

(72) Inventors: Hiroto Matsuoka, Tokyo (JP); Nobuaki Matsuura, Tokyo (JP); Kei Kuwabara, Tokyo (JP); Yuki Hashimoto, Tokyo (JP); Takako Ishihara, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 185 days.

(21) Appl. No.: 17/628,804

(22) PCT Filed: Jul. 22, 2019

(86) PCT No.: PCT/JP2019/028598
§ 371 (c)(1),
(2) Date: Jan. 20, 2022

(87) PCT Pub. No.: WO2021/014521
PCT Pub. Date: Jan. 28, 2021

(65) Prior Publication Data
US 2022/0264964 A1 Aug. 25, 2022

(51) Int. Cl.
*G01N 27/22* (2006.01)
*A41D 1/00* (2018.01)
(Continued)

(52) U.S. Cl.
CPC ............ *A41D 1/002* (2013.01); *A61B 5/6805* (2013.01); *G01N 27/223* (2013.01); *G01W 1/17* (2013.01)

(58) Field of Classification Search
CPC ...... A41D 1/002; A41D 1/005; A61B 5/6804; A61B 5/6805; A61B 5/6806; A61B 5/6807
See application file for complete search history.

(56) References Cited

U.S. PATENT DOCUMENTS

2008/0117950 A1* 5/2008 Braatz .................. G01J 5/02
374/E1.018
2016/0081622 A1* 3/2016 Abreu .................. A61P 9/04
600/549

(Continued)

FOREIGN PATENT DOCUMENTS

CN 204169990 U * 2/2015
CN 204169990 U 2/2015
(Continued)

OTHER PUBLICATIONS

Kwon, J. et al., "Evaluation of the Wet Bulb Globe Temperature (WBGT) Index for Digital Fashion Application in Outdoor Environments", Journal of the Ergonomics Society of Korea, Jan. 2017, vol. 36, Issue 1, p. 23-36.

(Continued)

*Primary Examiner* — Herbert K Roberts
(74) *Attorney, Agent, or Firm* — Slater Matsil, LLP

(57) ABSTRACT

A wearable device includes a sensor device and a clothes to which the sensor device is attached. The clothes includes a clothes body and an insertion and extraction portion that has an opening formed in the clothes body and enables the sensor device to be inserted into or extracted from the clothes body. The sensor device includes a humidity sensor configured to measure humidity in the clothes body and a housing having a first region exposed to an inside of the clothes body and a second region exposed to an outside of the clothes body, while the sensor device is inserted from the insertion and extraction portion into the clothes body. The humidity sensor is accommodated in the first region of the housing.

10 Claims, 10 Drawing Sheets

(51) Int. Cl.
*A61B 5/00* (2006.01)
*G01W 1/17* (2006.01)

(56) References Cited

U.S. PATENT DOCUMENTS

2016/0135743 A1 5/2016 Cobbett et al.
2021/0321682 A1* 10/2021 Ito .................... G05D 23/1931

FOREIGN PATENT DOCUMENTS

| JP | 2017538475 A | | 12/2017 |
| JP | 2018139899 A | * | 9/2018 |
| WO | WO-2020184686 A1 | * | 9/2020 |

OTHER PUBLICATIONS

Nippon Telegraph and Telephone Corp., "Use of sensor-equipped wear to combat heat and development of painting specifications to reduce maintenance costs of steel towers," Business Communication, vol. 56, No. 5, May 2019, pp. 13-15.

* cited by examiner

WEARABLE DEVICE, AND SENSOR DEVICE

CROSS-REFERENCE TO RELATED APPLICATION

This application is a national phase entry of PCT Application No. PCT/JP2019/028598, filed on Jul. 22, 2019, which application is hereby incorporated herein by reference.

TECHNICAL FIELD

The present invention relates to a wearable device and a sensor device, and particularly to a structure of a wearable device that monitors a thermal load on a human body.

BACKGROUND

In the related art, it is known that measuring the amount of solar radiation that a human body receives from the sun, and the temperature and humidity in clothes is effective in recognizing the comfort of clothes and preventing heatstroke.

A heat index (Wet Bulb Globe Temperature (WBGT)) is used as one of indices for measuring and evaluating such a hot environment. The heat index (WBGT) is an index focusing on the exchange of heat between the human body and the outside air, and incorporates three elements: humidity having a large effect on the heat balance of the human body, the thermal environment around a person such as solar radiation and radiation, and the temperature.

A WBGT meter in the related art that measures the heat index includes, for example, a black bulb temperature sensor, a temperature sensor, and a humidity sensor. These sensors measure a black bulb temperature, a wet bulb temperature, and a dry bulb temperature for calculating the heat index (WBGT) (see NPL 1).

The WBGT meter in the related art has a relatively large size. Thus, the heat index at a location where the WBGT meter is installed is measured. However, the heat balance of each user is largely influenced by the local environment in practice. For example, the amount of the solar radiation received by the user differs greatly depending on whether the user is outdoors, indoors, in the sun, or in the shade. Further, the temperature and the humidity in clothes also vary greatly depending on the clothes worn by the user, the movement state of the user, the perspiration state of the user, and the like. This influences the heat balance for each user.

Thus, it is important to accurately measure the amount of the solar radiation and the temperature and humidity in clothes for each user. For example, as illustrated in FIGS. 9 and 10, a small-sized sensor device 500 that measures the solar radiation and the temperature and the humidity in clothes for each user is developed. The sensor device 500 in the related art is attached to clothes 200 and used as a wearable device.

As illustrated in FIG. 9(a), a radiant heat sensor 520 is provided on a front surface 500a of the housing of the sensor device 500. As illustrated in FIG. 9(b), a temperature and humidity sensor 530 is provided on a rear surface 500b of the housing of the sensor device 500. A plurality of snap buttons 510 are arranged on the rear surface 500b such that the sensor device 500 can be attached to and detached from the clothes 200.

FIG. 9(c) illustrates the inside of the housing of the sensor device 500. A control board 540 configured to perform conversion into a signal indicating the amount of the solar radiation, and the temperature and the humidity inside the clothes, which are measured by the radiant heat sensor 520 and the temperature and humidity sensor 530 is provided. In a wearable device in the related art, as illustrated in FIG. 10, the sensor device 500 is attached to the outside of the clothes 200 with the two or more snap buttons 510, and the temperature and humidity sensor 530 measures the temperature and the humidity in the clothes 200 from a hole H formed in the clothes 200.

CITATION LIST

Non-Patent Literature

NPL 1: JuYoun Kwon, Ken Parsons, "Evaluation of the Wet Bulb Globe Temperature (WBGT) Index for Digital Fashion Application in Outdoor Environments", Journal of the Ergonomics Society of Korea, 2017, Vol. 36, Issue 1, p. 23-36 (14 pages)

SUMMARY

Technical Problem

However, in the wearable device in the related art, when the fabric of the clothes 200 to which the sensor device 500 is attached gets wet due to the sweat of a user or the like, it may not be able to accurately measure the humidity in the clothes due to the influence of water vapor generated from the fabric.

Specifically, in the wearable device in the related art, since the region of the clothes 200 to which the sensor device 500 is attached is covered by the housing, the air passage is blocked. Once the fabric is wetted, the region of the clothes 200 to which the sensor device 500 in the related art is attached do not dry easily. Thus, it takes a relatively long time for the temperature and humidity sensor 530 to be able to accurately measure the humidity in the clothes.

The embodiments of the present invention have been made in order to solve the above-described problems, and an object of the present invention is to provide a wearable device and a sensor device capable of accurately measuring the humidity in clothes.

Means for Solving the Problem

In order to solve the problems described above, according to an aspect of the present invention, a wearable device includes a sensor device, and clothes to which the sensor device is attached. The clothes includes a clothes body, and an insertion and extraction portion having an opening formed in the clothes body, the insertion and extraction portion enabling the sensor device to be inserted into or extracted from the clothes body. The sensor device includes a humidity sensor configured to measure humidity inside the clothes body, and a housing having a first region exposed to an inside of the clothes body and a second region exposed to an outside of the clothes body, while the sensor device is inserted from the insertion and extraction portion into the clothes body. The humidity sensor is accommodated in the first region of the housing.

In order to solve the problems described above, according to an aspect of the present invention, a sensor device includes a humidity sensor configured to measure humidity inside the clothes body, and a housing having a first region exposed to an inside of the clothes body and a second region exposed to an outside of the clothes body, while the sensor device is inserted into the clothes body. The humidity sensor is accommodated in the first region of the housing.

Effects of Embodiments of the Invention

According to embodiments of the present invention, a wearable device includes clothes having an insertion and extraction portion that enables a sensor device to be inserted into or extracted from the inside of a clothes body, and the sensor device includes a housing having a first region exposed to an inside of the clothes body and a second region exposed to an outside of the clothes body, while the sensor device is inserted into the clothes body from the insertion and extraction portion formed in the clothes body, in which a humidity sensor configured to measure humidity inside the clothes body is accommodated in the first region of the housing. Thus, it is possible to accurately measure the humidity inside the clothes.

DETAILED DESCRIPTION OF ILLUSTRATIVE EMBODIMENTS

Hereinafter, preferred embodiments of the present invention will be described in detail with reference to FIGS. 1 to 10.

Figure 1:
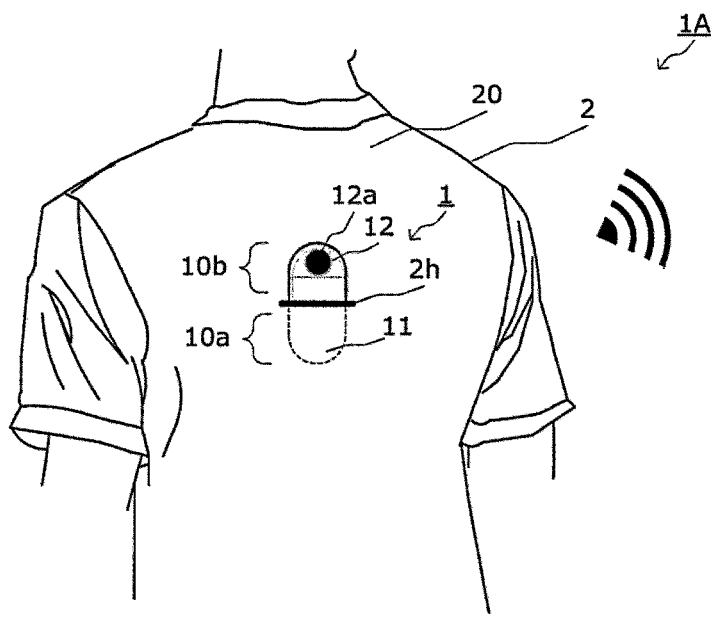
FIG. 1 is a view illustrating an example of a wearable device according to an embodiment of the present invention.

As illustrated in FIG. 1, a wearable device 1A according to the embodiment includes clothes 2 worn by a user and a sensor device 1 attached to the clothes 2. The sensor device 1 has a structure capable of being attached to the clothes 2, and measures radiant heat received by the user from the environment inside the clothes 2 and solar radiation.

Figure 2:
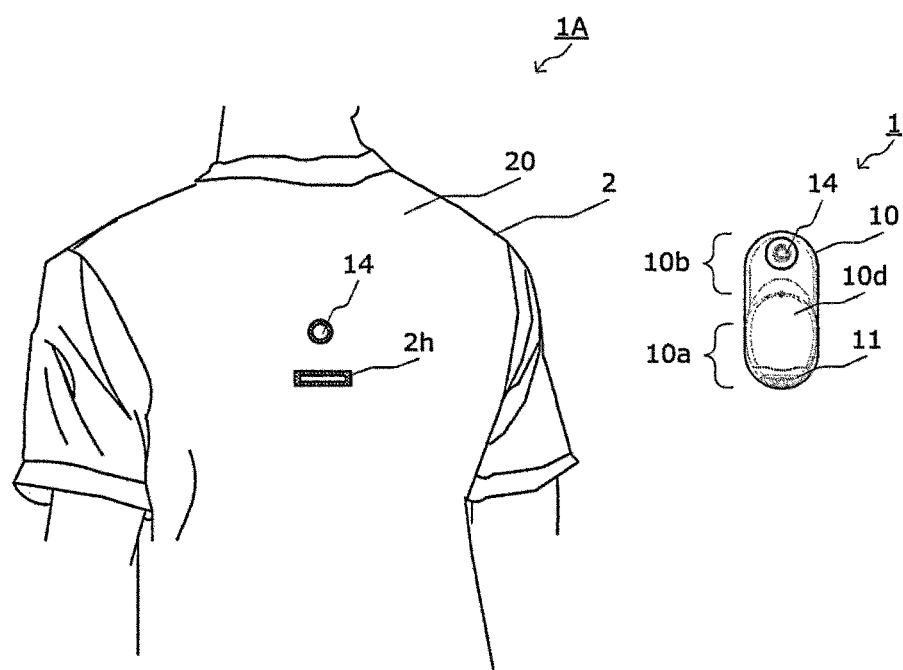
FIG. 2 is a view illustrating an example of the wearable device according to the embodiment.

The clothes 2 is, for example, a shirt including a clothes body 20 having a front body and a rear body, sleeves, and a collar, as illustrated in FIGS. 1 and 2. Further, examples of the clothes 2 also includes clothes such as a vest, compression shirts, jerseys, a tanktop, and an outerwear, in addition to the shirts. The clothes body 20 that is in contact with the user's torso may be formed of a stretchable fabric so as to appropriately fit to the user's body.

The outside of the clothes 2 and the clothes body 20 is a surface that is in contact with the outside air, and is hereinafter referred to as a "front surface 2a". The inner side of the clothes 2 and the clothes body 20 is a surface on a B side of the body of the user wearing the clothes 2, and is hereinafter referred to below as a "rear surface 2b".

As illustrated in FIG. 2, the clothes 2 has an opening formed in the clothes body 20 and has an insertion and extraction portion 2h enabling the sensor device 1 to be inserted into or extracted from the clothes body 20. The insertion and extraction portion 2h may be, for example, a cut having a length corresponding to the width of the sensor device 1 orthogonal to a direction in which the sensor device 1 is inserted and extracted. For the fabric surrounding the cut, a material that is stronger and more stretchable than the fabric of the clothes body 20 may be used. Alternatively, the insertion and extraction portion 2h may have strength by stitching the edge of a hole like a button hole with the thread.

The sensor device 1 is inserted from the insertion and extraction portion 2h into the clothes body 20 downward or upward along the rear surface 2b of the clothes body 20. "Upward" and "downward" are based on the ground. In the embodiment, an example in which the sensor device 1 is inserted downward from the insertion and extraction portion 2h into the clothes 2 and attached to the clothes body 20 will be described.

For example, a socket and a stud (e.g., female member) of a snap button 14 are provided on the clothes body 20 as a fixing member (e.g., second fixing member) at a position around the insertion and extraction portion 2h. The stud (e.g., male member) (e.g., first fixing member) of the snap button 14 is provided on a rear surface (e.g., outer surface) 10d of a housing 10 (described below) of the sensor device 1. The sensor device 1 is detachably attached to the clothes 2 by the snap button 14.

By detachably attaching the sensor device 1 to the clothes 2, after the wearable device 1A is used by the user, the sensor device 1 can be detached from the clothes 2 to wash only the clothes 2. Further, it is possible to prevent the sensor device 1 from being damaged due to getting set.

Figure 3:
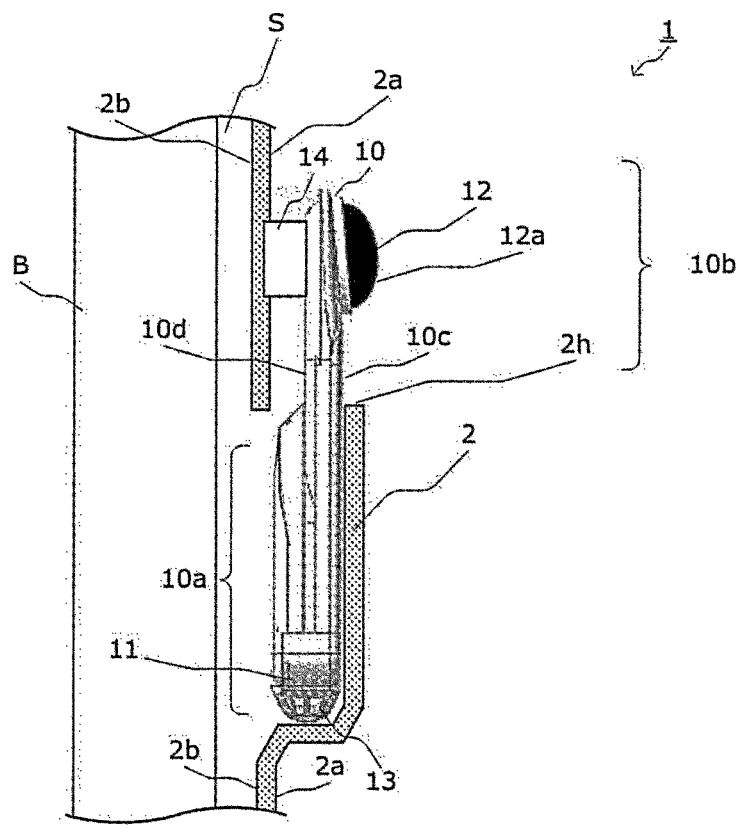
FIG. 3 is a view illustrating a specific example in which a sensor device according to the embodiment is attached to clothes.

The sensor device 1 is attached to the clothes body 20 such that the sensor device 1 is disposed, for example, from the center portion of the back of the user to the height of the scapula. When the sensor device 1 is attached at such a position, as illustrated in FIG. 3, an appropriate space s (hereinafter referred to as an "internal space S") is formed between the surface of the B side of the body of the user and a temperature and humidity sensor 11 described below. This is suitable for measurement of the temperature and humidity environment inside the clothes. The back is a portion of the body in which the amount of perspiration is relatively high. Thus, the back is suitable for measuring humidity in the clothes that sufficiently reflect the influence of the perspiration of the user.

Configuration of Sensor Device

The sensor device 1 includes the housing 10, a humidity sensor 11a that measures the humidity in the clothes body 20, a temperature sensor 11b that measures a temperature, and a radiant heat sensor 12 that measures a radiant heat from the outside of the clothes body 20. The humidity sensor 11a, the temperature sensor 11b, and the radiant heat sensor 12 are accommodated in the housing 10. Further, a control board 15 and a battery 16 that supplies power to the control board 15 are accommodated in the housing 10. In the embodiment, the temperature and humidity sensor 11 including the humidity sensor 11a and a temperature sensor 11b is used.

Figure 4:
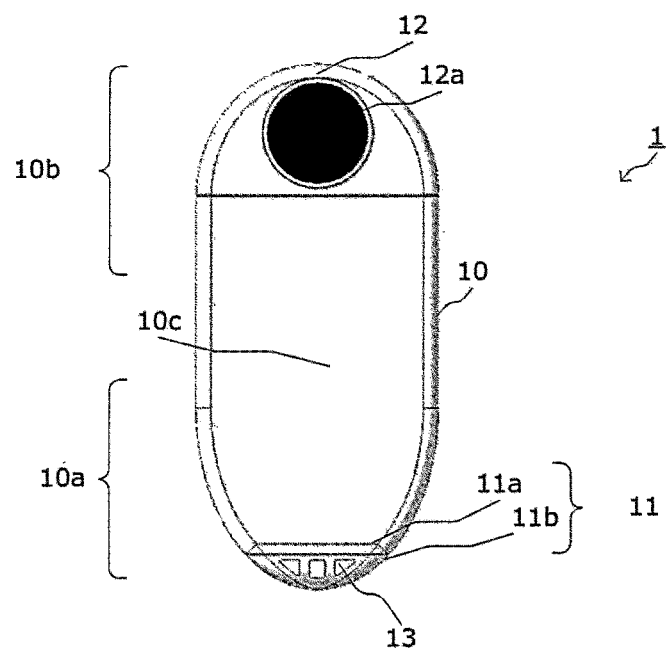
FIG. 4 is a schematic view of an appearance of the sensor device according to the embodiment of the present invention.
Figure 5:
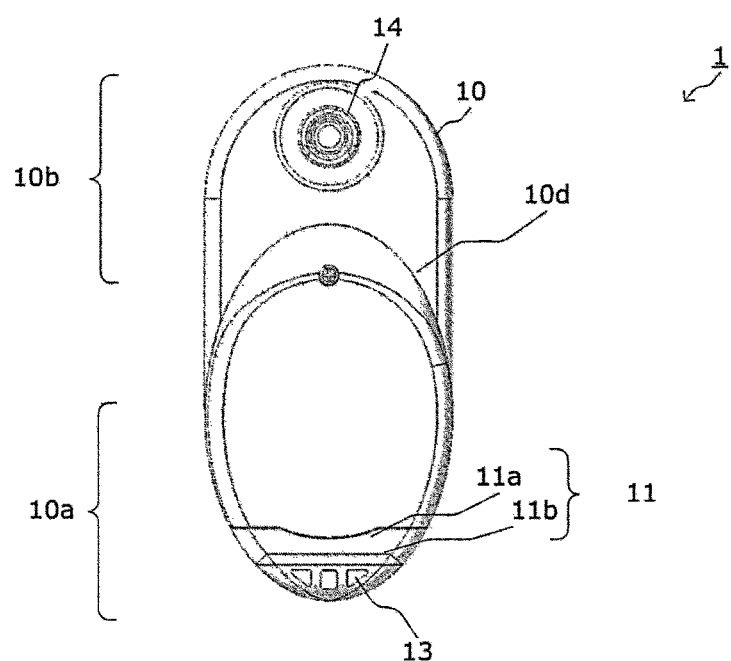
FIG. 5 is a schematic view of an appearance of the sensor device according to the embodiment of the present invention.
Figure 6:
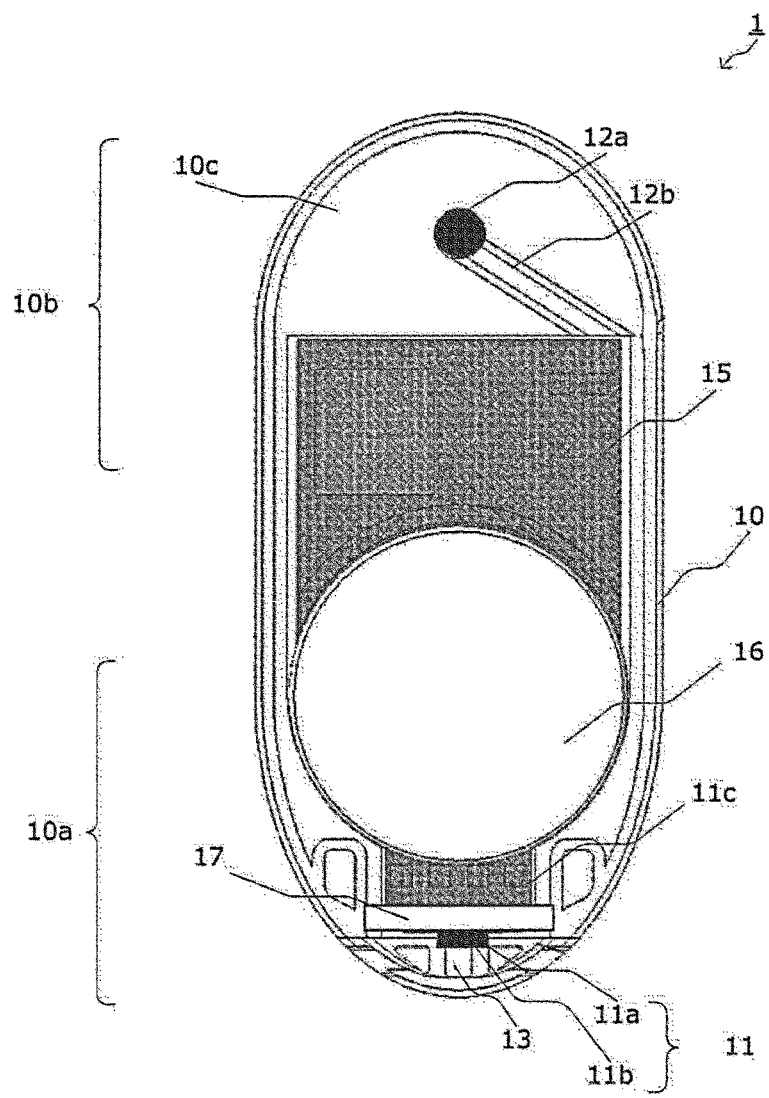
FIG. 6 is a schematic view of an internal structure of the sensor device according to the embodiment of the present invention.

The housing 10 is, for example, a container formed entirely in a flat and substantially-rectangular parallelepiped shape. The housing 10 has a front surface 10c and a rear surface 10d provided so as to face each other. As illustrated in FIGS. 4 to 6, the front surface 10c and the rear surface 10d of the housing 10 are formed, for example, in a rounded square shape when the housing 10 is viewed in plan view.

The housing 10 has a first region 10a exposed to the inside of the clothes body 20 and a second region 10b exposed to the outside of the clothes body 20. The first region 10a and the second region 10b are exposed while the housing 10 is inserted into the clothes body 20 from the insertion and extraction portion 2h formed on the clothes body 20. In the embodiment, the first region 10a included in the housing 10 is a region on one end side in the longitudinal direction of the housing 10, which is along a direction in which the sensor device 1 is inserted into and extracted from the inside of the clothes body 20 from the insertion and extraction portion 2h. The second region 10b included in the housing 10 is a region on the other end side in the longitudinal direction of the housing 10 in the direction in which the sensor device 1 is inserted into or extracted from the clothes body 20 from the insertion and extraction portion 2h.

The temperature and humidity sensor 11 is accommodated in the first region 10a of the housing 10. The radiant heat sensor 12 is accommodated in the second region 10b of the housing 10. As described above, the temperature and humidity sensor 11 and the radiant heat sensor 12 are accommodated in the housing 10 to be spaced from each other as illustrated in FIGS. 3, 4, and 5.

In the present embodiment, as illustrated in FIG. 5, the snap button 14 is provided on the rear surface 10d of the second region 10b of the housing 10.

A ventilation opening 13 is provided in the first region 10a of the housing 10. The ventilation opening 13 is provided adjacent to the temperature and humidity sensor 11, for example, as a grid-like cover. The ventilation opening 13 prevents the temperature and humidity sensor 11 from coming into direct contact with the surface of the body B of the user when the sensor device 1 is inserted into the clothes body 20. The ventilation opening 13 can ensure ventilation in the internal space S around the temperature and humidity sensor 11.

The housing 10 is formed of, for example, a polymer material such as acrylonitrile butadiene styrene (ABS) resin, rubber, or silicone resin. The housing 10 has a size of, for example, approximately 5 cm×3 cm×1 cm, and is formed such that the housing 10 can be attached to the user's clothes.

As illustrated in FIG. 6, the temperature and humidity sensor 11 is disposed in the first region 10a of the housing 10 via a heat insulating material 17. More specifically, the heat insulating material 17 is disposed between the temperature and humidity sensor 11 and a temperature and humidity sensor board 11c that detects a temperature and a humidity. The temperature and humidity sensor board 11c is electrically connected to the control board 15. The heat insulating material 17 may thermally separate the housing 10 from the temperature and humidity sensor 11.

The temperature and humidity sensor 11 is, for example, a sensor in which the electrostatic capacitive humidity sensor 11a and the temperature sensor 11b such as a semiconductor temperature sensor are integrally provided in one IC chip. Alternatively, for example, a thermistor or the like can be used as the temperature sensor 11b. The temperature and the humidity of the internal space S of the clothes 2, which are measured by the temperature and humidity sensor 11 are converted into a signal indicating the temperature and humidity inside the clothes by a processor 102 included in the control board 15 described below.

The radiant heat sensor 12 includes a black plate 12a having a black surface and a thermistor 12b as the temperature sensor. As illustrated in FIG. 6, the thermistor 12b is disposed so as to come into contact with the rear surface of the black plate 12a of the radiant heat sensor 12. The thickness of the black plate 12a of the radiant heat sensor 12 may take into consideration the time response and noise due to heat capacity. The surface area of the black plate 12a is a preset area.

As illustrated in FIGS. 3 and 4, the black plate 12a included in the radiant heat sensor 12 is exposed to the outside from the front surface 10c of the housing to in the second region 10b of the housing 10 and comes into contact with the outside air. The surface of the black plate 12a can be blackened with, for example, iron oxide so as to absorb radiant heat (thermal radiation) from sunlight or the like as much as possible. For example, a matte blackened surface is formed.

As illustrated in FIG. 4, the black plate 12a is formed in a disc shape in plan view, for example, and fits into a hole provided in the front surface 10c of the housing 10. The black plate 12a may be a spherical plate as illustrated in FIG. 3, instead of a flat plate. By having the black plate 12a having a spherical plate that protrudes to the outside, it is possible to absorb more radiant heat such as solar radiation than when a flat plate is used.

As illustrated in FIG. 6, the thermistor 12b is provided on the rear surface of the black plate 12a of the radiant heat sensor 12. The thermistor 12b is used as a temperature sensor that detects the temperature of the black plate 12a. The resistance value detected by the thermistor 12b is converted into a signal indicating the temperature of the black plate 12a by the processor 102 mounted on the control board 15, and then is output.

As described above, when electromagnetic waves emitted from the sun or the like reach the surface of the black plate 12a of the radiant heat sensor 12, the electromagnetic waves are converted to internal energy, and the temperature of the black plate 12a changes. The temperature of the black plate 12a increases in response to solar radiation and radiation received and absorbed by the black plate 12a. The thermistor 12b can measure radiant heat from the outside of the clothes 2 by measuring the temperature of the black plate 12a.

The control board 15 includes the processor 102 and controls the operation of the temperature and humidity sensor 11 and the radiant heat sensor 12. More specifically, the processor 102 calculates the humidity and the temperature inside the clothes which are measured by the temperature and humidity sensor 11, and the radiant heat temperature measured by the radiant heat sensor 12 and outputs the calculated values to the outside.

As the battery 16, for example, various batteries such as button-type lithium batteries and lithium air batteries can be used. The battery 16 supplies power to the control board 15.

Configuration Example of Control Board

Next, a configuration example of the control board 15 will be described with reference to the block diagram of FIG. 7.

Figure 7:
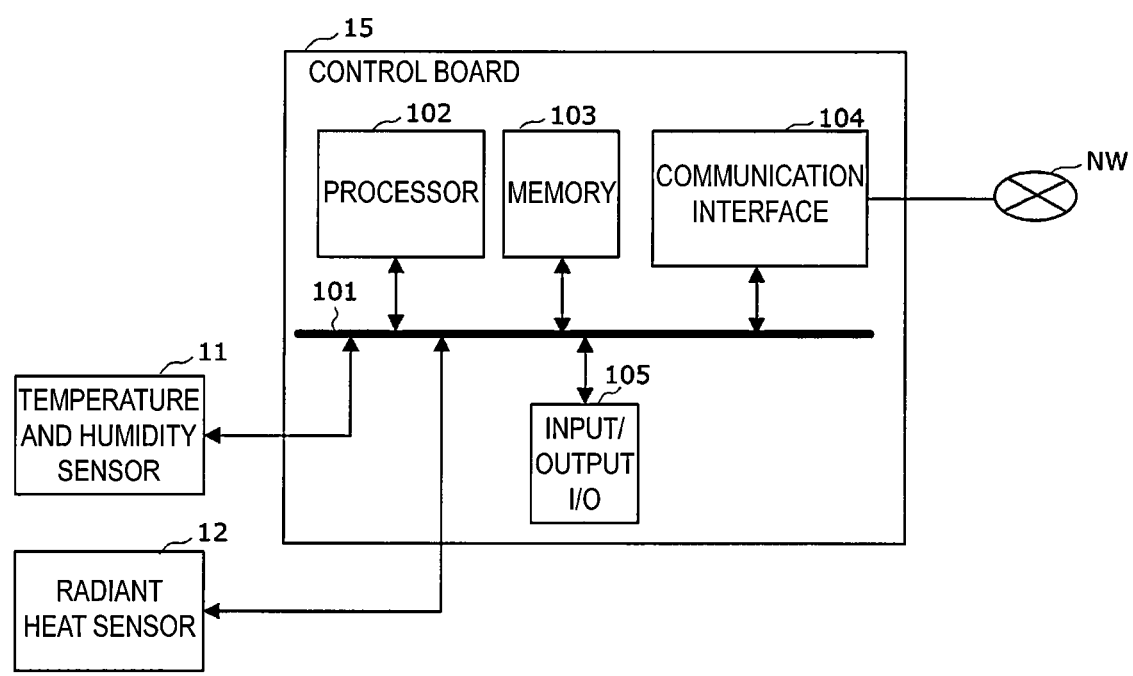
FIG. 7 is a block diagram illustrating an example of a hardware configuration of a control board according to the embodiment.

As illustrated in FIG. 7, the control board 15 may be realized by, for example, a computer including the processor 102 such as a microprocessing unit (MPU), a memory 103, a communication interface 104, and an input/output (I/O)

105, and a program for controlling these hardware resources. The processor 102, the memory 103, the communication interface 104, and the I/O 105 are connected to each other via a bus 101. The control board 15 includes an amplifier circuit, an analog-to-digital (A/D) converter, and the like, which are not illustrated. The control board 15 is connected to the temperature and humidity sensor 11 and the radiant heat sensor 12 via the bus 101.

A program for causing the processor 102 to perform various controls or calculations is stored in the memory 103 in advance. The memory 103 has a region for recording calibration data of the temperature and humidity sensor 11 and the radiant heat sensor 12.

The communication interface 104 is a communication control circuit for performing communication with various external electronic devices via a communication network NW. The temperature inside the clothes, the humidity inside the clothes, and the radiant heat from the outside, which are converted by the processor 102, are transmitted from the communication interface 104 to an external communication terminal device, an external server, or the like via the communication network NW.

For example, a communication control circuit and an antenna compatible with a wireless data communication standard such as LTE, 3G, 5G, wireless LAN, Bluetooth (trade name), or Low Energy are used as the communication interface 104.

The I/O 105 includes an I/O terminal that receive an input of a signal from an external device or outputs a signal to the external device.

Mounting Example of Sensor Device

Here, a mounting example of the sensor device 1 having the above-described configuration onto the clothes body 20 will be described with reference to FIG. 3. For example, the sensor device 1 is inserted into the clothes 2 from the insertion and extraction portion 2h formed in the clothes 2 and having a cut-out shape. In this case, the rear surface 10d of the housing 10 is on the B side of the body of the user, and the front surface 10c of the housing 10 is on the outside air side.

More specifically, the lower half of the rear surface 10d of the housing 10 on the ground side, that is, the first region 10a in which the temperature and humidity sensor 11 is accommodated, comes into contact with the internal space S of the clothes 2. A portion of the ventilation opening 13 provided in the first region 10a of the housing 10 covering the temperature and humidity sensor 11 comes into contact with the rear surface 2b of the clothes 2. In this manner, the temperature and humidity sensor 11 directly comes into contact with the internal space S of the clothes 2.

On the other hand, the upper half of the rear surface 10d of the housing 10 on the opposite side of the ground including the second region 10b comes into contact with the front surface 2a of the clothes 2 via the snap button 14.

The lower half of the front surface 10c of the housing 10 including the first region 10a is in contact with the rear surface 2b in the clothes 2. On the other hand, the upper half of the front surface 10c of the housing 10 including the second region 10b is in contact with the outside air. That is, the radiant heat sensor 12 is exposed to the outside air.

In this manner, the sensor device 1 is detachably fixed to the clothes 2 by the snap button 14, and the front surface 10c of the lower half of the housing 10 inserted into the clothes 2 comes into contact with the rear surface 2b of the clothes 2 to support the weight of the sensor device 1. When the sensor device 1 is mounted on the clothes 2, the temperature and humidity sensor 11 come into direct contact with the internal space S of the clothes 2 to measure the temperature and the humidity inside the clothes 2. At the same time, the radiant heat sensor 12 exposed to the outside of the clothes 2 can measure radiant heat received from the outside by the user wearing the clothes 2.

In the present embodiment, for example, the sensor device 1 is inserted into the clothes 2 from the insertion and extraction portion 2h formed in the clothes 2 and having a cut-out shape. At this time, because the clothes 2 functions like a pocket to support the weight of the sensor device 1, it is possible to reduce the number of the snap buttons 14, and the sensor device 1 and the clothes 2 can be easily attached and detached. As described above, when the fabric around the cut-out is stronger and more stretchable than the fabric of the clothes body 20, the cut-out becomes like a band and can support the weight of the sensor device 1.

Figure 10:
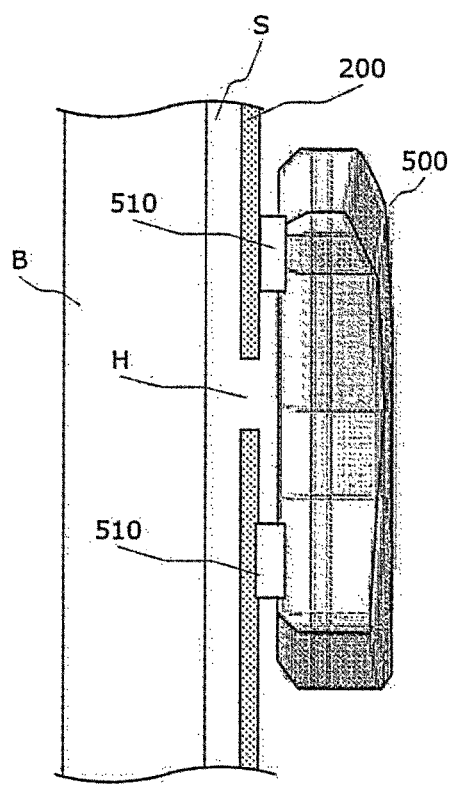
FIG. 10 is a view illustrating a specific example of a wearable device in which the sensor device in the related art is attached to clothes.

As described above, in the sensor device 500 in the example in the related art, as illustrated in FIG. 10, the entirety of the sensor device 500 is provided outside the clothes 200. In the sensor device 500 in the example in the related art, for example, in a case where the user has a backpack or the like, there is a possibility that the sensor device 500 is caught by the backpack itself or a strap, such as a shoulder harness, attached to the backpack, and thus is detached from the clothes 200.

However, in the sensor device 1 according to the embodiment, because the lower half of the housing 10 is covered by the clothes 2 as illustrated in FIGS. 1 and 3, it is possible to prevent, when the user wears the wearable device 1A, the sensor device 1 from being detached from the clothes 2 due to an external impact such as a backpack.

Figure 8:
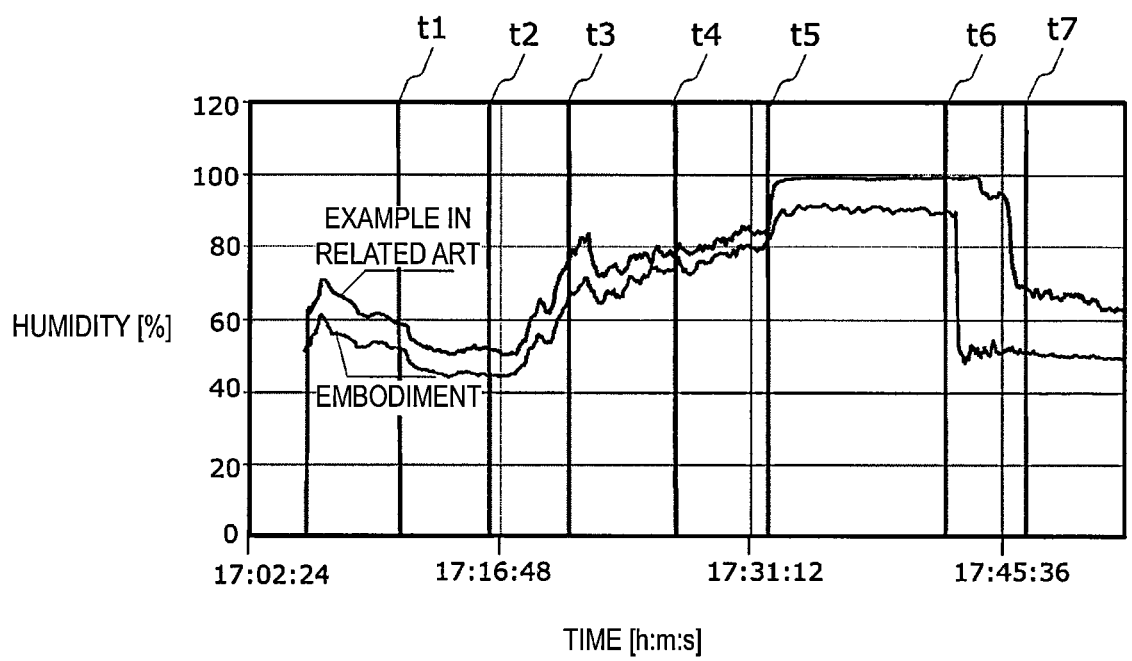
FIG. 8 is a diagram for describing effects of the wearable device according to the embodiment.

Next, the effects of the wearable device 1A according to the present embodiment will be described with reference to FIG. 8. FIG. 8 illustrates the humidity inside the clothes that is measured when a test subject wears the wearable device 1A according to the present embodiment, and the humidity in the clothes that is measured when the test subject wears a wearable device including the sensor device 500 in the related art. In FIG. 8, the horizontal axis indicates the elapsed time, and the vertical axis indicates the measured value of the humidity.

Figure 9:
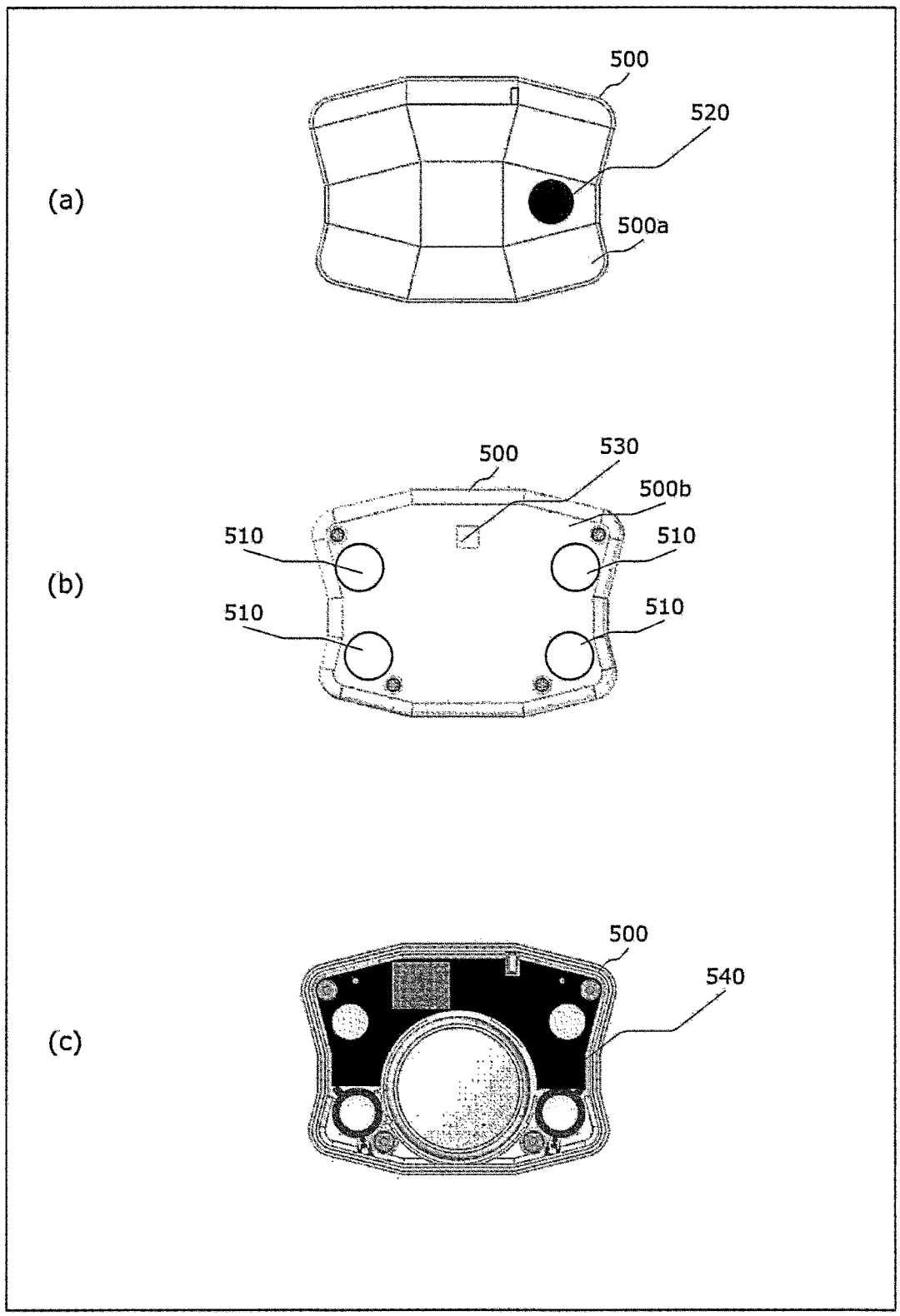
FIG. 9 is a schematic view illustrating an example of a sensor device in the related art.

The wearable device including the sensor device 500 in the related art is mounted on the outside of the clothes 200 by a plurality of snap buttons 510, as illustrated in FIGS. 9 and 10. In the wearable device in the related art, as illustrated in FIG. 10, a temperature and humidity sensor 530 accommodated in a housing of the sensor device 500 measures the humidity inside the clothes 200 in the internal space S from a hole H provided with the clothes 200.

In the measurement example, the test subject wore each of the wearable device 1A according to the present embodiment and the wearable device in the related art, and then ran on a treadmill. The running speed of the treadmill was set to gradually increase from a static state at time t1. Specifically, the running speed was 6 [km/h] at time t2, 8 [km/h] at time t3, and 10 [km/h] at time t4. Then, the treadmill was stopped at time t5, and the running speed was set to be a static state for a predetermined period until time t6. Then, the test subject was exposed to the wind of an electric fan with the clothes 2 wet with sweat, for a period of time from the time t6 to time t7.

As illustrated in FIG. 8, in the wearable device in the related art, the measured humidity value is higher than the value of the humidity measured by the wearable device 1A according to the present embodiment throughout the measurement period. In addition, since the test subject began to sweat as the running speed of the treadmill was increased from the time t1 to the time t5, both of the value of the humidity measured in the related art and the value of the humidity measured in the present embodiment were increased.

When the treadmill was stopped at the time t5, the test subject sweated at once, and the entire clothes 2 got wet with sweat. At this time, the values of the humidity measured in the example in the related art and in the present embodiment were the highest values. When the test subject was exposed to the wind of an electric fan at the time t6, the sweat of the test subject was pulled and the clothes 2 were also dried. Thus, in the present embodiment, the measured humidity value dropped at once. However, in the example in the related art, the humidity value was still high, and it took a time to lower the humidity value.

That is, in the sensor device 500 in the related art, the rear surface 500b of the housing is shaped like a wall, and the area around the temperature and humidity sensor 530 accommodated in the housing is not well ventilated, such that the measured humidity is higher than the actual value. On the other hand, in the wearable device 1A according to the present embodiment, the first region 10a of the housing to in which the temperature and humidity sensor 11 is accommodated is inserted into the clothes 2, and the first region 10a comes into direct contact with the internal space S. Thus, the ventilation around the temperature and humidity sensor 11 is ensured. Thus, the wearable device 1A can measure the humidity inside the clothes more accurately as compared with the example in the related art.

As described above, in the wearable device 1A according to the embodiment, in the sensor device 1, the first region 10a of the housing 10 in which the temperature and humidity sensor 11 is accommodated is inserted into the clothes body 20 from the insertion and extraction portion 2h having an opening formed in the clothes body 20. Thus, in the wearable device 1A, it is possible to suppress mixing of water vapor components contained in the fabric of the clothes 2 and more accurately measure the humidity in the clothes.

In the wearable device 1A according to the embodiment, in the sensor device 1, the second region 10b of the housing 10 in which the radiant heat sensor 12 is accommodated is exposed to the outside of the clothes body 20. Thus, in the wearable device 1A, it is possible to measure radiant heat, such as solar radiation, which the user receives from the outside, in addition to the further accurate measurement of the humidity and the temperature in the clothes. Thus, in the wearable device 1A, it is possible to more accurately measure a different hot environments for each user, and to take individual measures against heat stroke based on the heat index of each user.

Further, in the wearable device 1A according to the present embodiment, the lower half of the sensor device 1 including the first region 10a of the housing 10 is inserted into the clothes 2, and the clothes 2 functions as a pocket to support the weight of the sensor device 1. Consequently, it is possible to reduce the number of the snap buttons 14. Thus, in the wearable device 1A, the sensor device 1 can be easily attached to and detached from the clothes 2, and also the sensor device 1 and the clothes 2 are stably fixed.

In the above-described embodiment, a case where the snap button 14 is used as a fixing member that detachably fixes the sensor device 1 and the clothes 2 has been described. However, the fixing member is not limited to the snap button 14 as long as the sensor device 1 and the clothes 2 can be detachably fixed to each other. For example, a surface fastener may be used instead of the snap button 14.

In the above-described embodiment, the case where the snap button 14 is provided has been described, but the snap button 14 may be used as necessary. For example, the snap button 14 can be omitted when the periphery of a cut-out of the insertion and extraction portion 2h is formed of a band-like and stretchable fabric or material such that the insertion and extraction portion 2h supports the weight of the sensor device 1.

Hitherto, although the wearable device and the sensor device according to the embodiment of the present invention has been described above, the present invention is not limited to the above-described embodiment and can be modified into various forms that can be conceived by a person skilled in the art within the scope of the invention described in the claims.

REFERENCE SIGNS LIST

1 Sensor device
1A Wearable device
2 Clothes
20 Clothes body
10c, 2a Front surface
10d, 2b Rear surface
2h Insertion and extraction portion
10 Housing
10a First region
10b Second region
11 Temperature and humidity sensor
11a Humidity sensor
11b Temperature sensor
11c Temperature and humidity sensor board
12 Radiant heat sensor
12a Black plate
12b Thermistor
13 Ventilation opening
14 Snap button
15 Control board
16 Battery
17 Heat insulating material
101 Bus
102 Processor
103 Memory
104 Communication interface
105 Input/output (I/O)

The invention claimed is:

1. A wearable device comprising:
a sensor device; and
clothes to which the sensor device is attached,
wherein the clothes comprise:
 a clothes body; and
 an insertion and extraction portion comprising an opening in a panel of the clothes body, the panel of the clothes body having an inner surface exposed to an interior region of the clothes body and an outer surface exposed to an outside environment, the insertion and extraction portion enabling the sensor device to be inserted into or extracted from the clothes body;
wherein the sensor device comprises:
 a humidity sensor configured to measure a humidity inside the clothes body;
 a radiant heat sensor configured to measure radiant heat from the outside environment; and
 a housing comprising a first region and a second region, wherein, in a state in which the sensor device is inserted into the opening and detachably attached to the clothes, the first region is disposed along and in physical contact with the inner surface of the panel of the clothes body and the second region is disposed along and in physical contact with the outer surface of the panel of the clothes body, wherein the humidity sensor is accommodated in the first region of the housing and the radiant heat sensor is accommodated in the second region of the housing.

2. The wearable device of claim 1, wherein the sensor device further comprises a first fixing member provided on an outer surface of the housing, the clothes further comprise a second fixing member provided on the clothes body, and the first fixing member and the second fixing member are detachably fixed to each other.

3. The wearable device of claim 1, wherein the sensor device further comprises a temperature sensor configured to measure a temperature inside the clothes body, and the temperature sensor is accommodated in the first region of the housing.

4. The wearable device of claim 1, wherein the sensor device further comprises:
   a control board configured to control an operation of a sensor comprising the humidity sensor, and to output, to an outside, sensor data comprising humidity inside the clothes, the humidity being measured by the humidity sensor, and
   a battery configured to supply power to the control board.

5. A sensor device detachably attached to clothes comprising a clothes body, the sensor device comprising:
   a humidity sensor configured to measure a humidity inside the clothes body;
   a radiant heat sensor configured to measure radiant heat from an outside of the clothes body; and
   a housing comprising a first region and a second region, wherein, in a state in which the sensor device is inserted into an opening in a panel of the clothes body and detachably attached to the clothes, the first region is disposed along and in physical contact with an inner surface of the panel of the clothes body that is exposed to an interior region of the clothes body and the second region is disposed along and in physical contact with an outer surface of the panel of the clothes body that is exposed to an outside environment, wherein the humidity sensor is accommodated in the first region of the housing and the radiant heat sensor is accommodated in the second region of the housing.

6. A wearable device comprising:
   a clothes body; and
   a sensor device inserted in an insertion/extraction opening disposed in a panel of the clothes body and detachably attached to the clothes body, wherein the panel of the clothes body has an inner surface exposed to an interior region of the clothes body and an outer surface exposed to an outside environment, and wherein the sensor device comprises:
      a housing having a first end and a second end in a longitudinal direction of the housing, wherein a first region on the first end of the housing is disposed along and in physical contact with the inner surface of the panel of the clothes body and a second region on the second end of the housing is disposed along and in physical contact with the outer surface of the panel of the clothes body;
      a humidity sensor in the first region of the housing, the humidity sensor being adjacent to a ventilation opening in the first region of the housing;
      a radiant heat sensor in the second region of the housing; and
      a controller configured to measure humidity of an inside of the clothes body with the humidity sensor, to measure radiant heat of the outside of the clothes body environment with the radiant heat sensor, and to transmit the humidity and the radiant heat to an external device.

7. The wearable device of claim 6 further comprising:
   a fixing member detachably fixing the clothes body to the sensor device.

8. The wearable device of claim 7, wherein the fixing member is on a rear surface of the housing, and the radiant heat sensor comprises a black plate on a front surface of the housing.

9. The wearable device of claim 6, wherein the clothes body comprises a first fabric, a second fabric surrounds the insertion/extraction opening, and the second fabric is stronger and more stretchable than the first fabric.

10. The wearable device of claim 7, wherein a rear surface of the housing contacts the outer surface of the panel of the clothes body, and a front surface of the housing contacts the inner surface of the panel of the clothes body.

* * * * *